(12) United States Patent
Schwer et al.

(10) Patent No.: US 8,632,551 B2
(45) Date of Patent: Jan. 21, 2014

(54) RESETTING TOOL

(75) Inventors: Stefan Schwer, Lurrach (DE); Reto Babst, Kriens (CH); Orlando Martinelli, Herzogenbuchsee (CH)

(73) Assignee: Depuy Synthes Products, LLC, Raynham, MA (US)

( * ) Notice: Subject to any disclaimer, the term of this patent is extended or adjusted under 35 U.S.C. 154(b) by 1351 days.

(21) Appl. No.: 10/592,543

(22) PCT Filed: Jan. 19, 2005
(Under 37 CFR 1.47)

(86) PCT No.: PCT/IB2005/000130
§ 371 (c)(1),
(2), (4) Date: Jun. 10, 2008

(87) PCT Pub. No.: WO2005/092225
PCT Pub. Date: Oct. 6, 2005

(65) Prior Publication Data
US 2012/0041447 A1 Feb. 16, 2012

(30) Foreign Application Priority Data
Mar. 11, 2004 (WO) .................. PCT/IB2004/000677

(51) Int. Cl.
| | |
|---|---|
| A61B 17/58 | (2006.01) |
| A61B 17/60 | (2006.01) |
| A61F 2/00 | (2006.01) |
| A61B 17/80 | (2006.01) |
| A61B 17/70 | (2006.01) |
| A61B 17/68 | (2006.01) |

(52) U.S. Cl.
USPC ........ 606/105; 606/292; 606/86 A; 606/86 B; 606/281; 606/282

(58) Field of Classification Search
USPC ........ 606/86 B, 86 A, 105, 281, 292; 411/435
See application file for complete search history.

(56) References Cited

U.S. PATENT DOCUMENTS

| | | | | | |
|---|---|---|---|---|---|
| 2,355,679 | A | * | 8/1944 | Roxs et al. ................ | 411/432 |
| 4,611,581 | A | * | 9/1986 | Steffee ..................... | 606/292 |
| 4,655,199 | A | * | 4/1987 | Steffee ..................... | 606/246 |
| 4,696,290 | A | * | 9/1987 | Steffee ..................... | 606/286 |

(Continued)

FOREIGN PATENT DOCUMENTS

| | | |
|---|---|---|
| DE | 44 18 974 A1 | 5/1995 |
| EP | 0 465 866 A1 | 1/1992 |

OTHER PUBLICATIONS

International Search Report of PCT/IB2005/000130.

*Primary Examiner* — David Bates
(74) *Attorney, Agent, or Firm* — Fay Kaplun & Marcin, LLP

(57) ABSTRACT

The invention relates to a resetting tool (1a), for the axial displacement of a Kirschner wire (2a), in particular, for application with bone plates, which may be implanted for the fixing of fractures. The above comprises a Kirschner wire (2a), comprising a thread in at least a part region and at least one guide tube (4a, 4b), by means of which the Kirschner wire may be positioned. A nut (3a) is provided, which is slotted and contains an internal drilling, such that the nut may be placed over the Kirschner wire and may be supported on the guide tube, whereby the Kirschner wire may be displaced in the axial direction by means of rotation of the nut.

15 Claims, 3 Drawing Sheets

(56) References Cited

U.S. PATENT DOCUMENTS

| | | | |
|---|---|---|---|
| 4,790,297 A * | 12/1988 | Luque | 606/86 A |
| 5,458,604 A | 10/1995 | Schmieding et al. | |
| 5,993,450 A | 11/1999 | Worcel | |
| 6,015,413 A | 1/2000 | Faccioli et al. | |
| 6,402,757 B1 | 6/2002 | Vandewalle et al. | |
| 6,821,070 B1 * | 11/2004 | Thompson | 411/433 |
| 2002/0143335 A1 * | 10/2002 | von Hoffmann et al. | 606/67 |
| 2004/0097941 A1 * | 5/2004 | Weiner et al. | 606/72 |

\* cited by examiner

RESETTING TOOL

The invention relates to a resetting tool and a nut for a resetting tool for the axial displacement of a Kirschner wire.

Kirschner wires are frequently used in the fixation of fractures. They often serve only for temporary fixation and stabilization, while the permanent fixation required for bone healing is ensured, for example by bone screws. Furthermore, they are used in the resetting of the fracture. In these cases, the Kirschner wires must be removed after the treatment.

An example of such a fracture treatment may be explained with reference to the less invasive stabilization system (LISS). A characteristic of this system is that a plate-like implant together with locking screws acts internally as a so-called fixateur. An advantage of the system is that the blood supply to the bone under the plate is maintained since in principle no contact or only very slight contact is necessary and occurs between the plate implant and bone. Load transmission elements are the screws which are locked in the plate, in combination with the plate itself. However, the plate implant must be positioned comparatively close to the bone, and it is for this reason that such implants are as a rule anatomically pre-shaped. For positioning the implant, only a comparatively small incision in the tissue is required so that the plate can be inserted between bone and soft tissues. The locking is then effected by means of further small incisions through the skin from outside.

Kirschner wires are used in this system for the preliminary fixation and connection of the plate-like implant with the bone. For this purpose, the Kirschner wires are introduced and subsequently removed and are replaced by corresponding locking screws. Kirschner wires are also useful for resetting a fracture. After resetting the locking screws are introduced and the Kirschner wire is removed again. Consequently, it is important that a Kirschner wire is not only introduced in the bone but also removed from it again. Various tools are provided for this purpose in the prior art. Thus, U.S. Pat. No. 6,015,413 discloses a device for extracting wires which have a thread. The device is similar to pliers so that the wire can be gripped. The traction on the Kirschner wire is exerted by mechanically forcing apart the two halves of the pliers, with the result that a shortening is achieved which is finally converted into a traction movement. The traction movement of this device is, however, comparatively coarse. No guidance of the wire is provided. The Kirschner wire may be bent and twisted. In general, the traction movement is therefore unsatisfactory.

DE-A1-44 18 974 and EP-A1-0 465 866 each disclose special wires for which in each case a special extraction means is then provided. Thus, the German Laid-Open Application describes a compression thread drilling wire over which a clamping nut is pushed. The compression of the wire is produced by turning the clamping nut. The clamping nut disclosed therein can be used only for the special wire disclosed in the publication. The European Patent Application describes a wire for a fixateur for setting up, fixing and regulating the clamping position of bone segments. The wire is formed in a very special manner and has a plurality of different sections. A so-called retaining means which serves for holding the drilling head and hence performs a protective function can be mounted on a particular section of this wire. By axial displacement of the retaining means, the wire can finally be released from its anchoring. Application to the Kirschner wire and the removal thereof, for example in the fixation by means of LISS, is not possible.

Furthermore, a traction instrument is known for use in the LISS technique. Here, a specially formed Kirschner wire, the traction wire, is inserted into a guide. The traction wire has a drill tip and a bone thread in the front region and a standard thread in the rear region. A tension nut by means of which the axial displacement of the tension device is effected is provided on this standard thread. However, the fact that there is a limitation in depth due to the two different threads which are to be provided on the device is disadvantageous. Another disadvantage is that the tension nut has to be moved a large distance over the standard thread before the guide is reached, where the traction movement can first take place.

It is therefore an object of the present invention to provide a resetting tool for the axial displacement of a Kirschner wire, with the aid of which a Kirschner wire can be displaced easily, reliably and as exactly as possible in the axial direction. A limitation in depth should as far as possible not occur. Furthermore, the resetting tool should be capable of being used as universally as possible.

The resetting tool according to the invention for displacing a Kirschner wire can be used in particular with bone plates which are implantable for the fixation of fractures. It comprises a Kirschner wire which has a thread, in particular a bone thread, at least in a partial region. The bone thread may be, for example, a cortical or a cancellous bone thread. Furthermore, at least one guide tube which can be positioned over the Kirschner wire is provided. According to the invention, a nut which is slotted and has an inner bore is provided so that the nut can be mounted on the Kirschner wire and can be supported on the guide tube.

According to a first preferred working example, the nut is therefore open at one point so that there is a passage for the central bore of the nut. It has a continuous longitudinal slot. The nut is mounted in particular laterally. According to a second preferred working example, the nut has a transverse slot, a first longitudinal partial slot and a second longitudinal partial slot, which are connected to one another. The nut can thus be mounted on the wire by threading. The nut is thus connected to the wire in a stable manner like nuts known from the prior art, which are screwed on to the wire and have to be moved up to the guide tube by rotational movements.

The axial displacement of the Kirschner wire is achieved by rotational movement of the nut. As a result of the rotational movement, the position of the bone fragment in the axial direction can be controlled. Preferably, a continuous bone thread, in particular a cortical or cancellous bone thread, is provided on the Kirschner wire, which has numerous advantages. A depth limitation is thus ruled out. There is furthermore no need to provide different lengths of the Kirschner wire; instead, a single length would in principle be sufficient.

According to a first embodiment, the nut is mounted on the wire in the manner of a clip. This means that the two halves of the nut formed by the longitudinal slot are forced slightly apart so that the Kirschner wire can be introduced into the central bore via this longitudinal slot. In a preferred embodiment, a small incision which imparts a hinge function to the remaining wall is provided on the inside of the nut located opposite the longitudinal slot. Alternatively, this slight opening of the nut is facilitated by a preferably springy hinge.

According to a second embodiment, the mounting of the nut is effected by means of bayonet-like threading of the wire through the guide slots of the nut. For this purpose, the nut has a horizontal or transverse slot and two longitudinal slots executed partially, referred to as partial longitudinal slots. The wire is threaded on by insertion into the transverse slot and subsequent rotational movement, so that it enters the partial longitudinal slot.

As a result of the nut design according to the invention, said nut can be mounted at any desired point of the Kirschner wire.

Threading from the end of the Kirschner wire, as is necessary in the case of the nuts in the prior art, is dispensed with.

The nut is preferably made of plastic, in particular polyethylene. Consequently, the nut is cheap to produce and can be provided for use only once. Preferably, the nut is destroyed by a sterilization process, for example the steam sterilization customary in hospitals. The glass transition temperature of the plastic used is therefore preferably below the sterilization temperature, usually about 150° C., in hospitals. This not only ensures that the nut is used only once but also that the Kirschner wire can be used only once. If the nut partially melts in the steam sterilization process, it sticks to the wire, with the result that said wire too cannot be reused. This ensures that not only the nut but also the Kirschner wire can be used only once, which is advantageous in particular owing to the poorly accessible spaces between wire and nut. The resetting tool can furthermore be delivered in a sterile pack ready for use, to be used only once.

Furthermore, the inner bore of the nut may have a thread. This may likewise be a bone thread or a symmetrical thread in the manner of a metric thread. The symmetrical thread has the advantage that the nut can be mounted in any desired direction on the Kirschner wire; it then has no preferred direction. In contrast, a sawtooth-shaped bone thread has a preferred direction so that, when mounting the nut, it is necessary to ensure that this is taken into account. In principle, however, there is no need at all for a thread since the bone thread of the Kirschner wire can itself form a thread in the inner bore of the nut as a result of the rotational movement.

The drawings are described below with reference to a PHILOS® plate system (Proximal Humerus Internal Locking System) from Synthes®. However, the invention is not limited thereto but is in fact also open to other osteosynthesis areas in which a Kirschner wire with bone thread or the like is used and where said wire has to be removed again, in particular in an LISS fixation.

The resetting tool is consequently also used in other fixation techniques for fractures. The patent claims are accordingly to be interpreted broadly. PHILOS® is used in particular in the case of dislocated fragmentary fractures of the proximal humerus. Similar to LISS, which is used in the case of fractures of the proximal lateral tibia and of the distal femur, an anatomically pre-shaped implant is provided which, in combination with the locking screws, bears the load.

The list of reference numerals and the drawings, together with the articles described or protected in the patent claims, are an integral part of the disclosure of this Application.

DESCRIPTION OF FIGURES

The figures are described in relation to one another and as a whole. Identical reference numerals denote identical components; reference numerals with different indices indicate functionally identical components.

FIG. 1 shows the resetting tool 1a in its intended use. It is introduced into a drill guide 9a of an aiming device 8. The aiming device 8 is fixed on the implant 7 with the aid of a screw 11. The implant 7 is plate-like and has a plurality of bores 10 though which locking screws can be inserted and with the aid of which the fixation of bone is carried out. The implant 7 remains in the body at least until the fracture has healed. It is the opposite situation to the aiming device 8, which is mounted only temporarily on the implant 7. The aiming device 8 has numerous drill guides 9. With the aid of the drill guides 9, the locking screws are introduced. The aiming device serves here as a guide and positioning aid. As is evident from FIG. 1, the resetting tool 1a is inserted into such a drill guide 9a.

Figure 1:
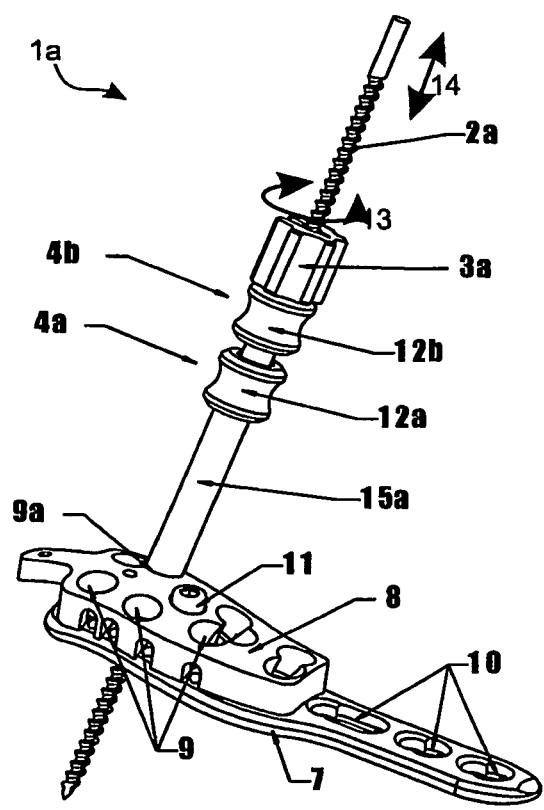
FIG. 1 shows the resetting tool according to the invention in use according to the invention in a schematic perspective diagram.

The resetting tool 1a has a Kirschner wire 2a. Preferably, the Kirschner wire 2a is made of steel. This is introduced through at least one guide tube 4. In the working example of FIG. 1, two guide tubes 4a, 4b are provided. The guide tubes 4 are sleeve-like. They have in each case a shaft 15 and a grip 12. The guide tubes are concentric and are introduced one into the other so that in each case only the grip area 12a, 12b is visible. Only in the case of guide tube 4a is the shaft 15a too visible over its total length. The guide tubes 4 perform different functions. Thus, for example, the guide tube 4a is the so-called tissue protection sleeve and the guide tube 4b is the so-called drill bush. The tissue protection sleeve also serves, for example, as an insertion sleeve for a locking screw and moreover for receiving a drill bush, the guide tube 4b. In the case of the PHILOS® system, the Kirschner wire according to the invention is additionally guided in the drill bush, i.e. in the guide tube 4b. In principle, however, it is sufficient for carrying out the invention if a single guide tube 4 is provided. The guide tube 4 is introduced into the drill guide 9a. The Kirschner wire 2a can now be introduced through the guide tube 4 and is axially displaceable therein.

For withdrawing the Kirschner wire 2a, a nut 3a according to the invention is mounted laterally via a slot 16. This nut 3a is supported on the guide tube 4 in the position of use. In the working example of FIG. 1, the nut is supported on the grip 12b of the guide tube 4b. By means of a rotational movement of the nut 3a, indicated by the arrow 13, the Kirschner wire 2a is displaced in the axial direction, indicated by the arrow 14. The axial displacement of a bone fragment moved by the Kirschner wire takes place in a direction towards the implant 7. After removal of the Kirschner wire 2a, a locking screw or the like can be set in its place.

Figure 2:
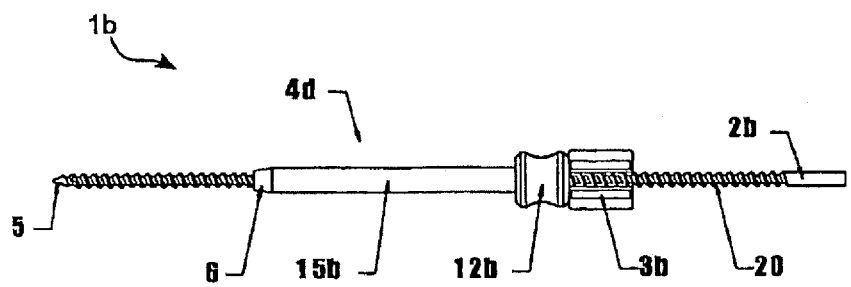
FIG. 2 shows a resetting tool according to the invention in a schematic plan view.

FIG. 2 schematically shows a resetting tool 1b according to the invention. The Kirschner wire 2b has a continuous thread, in the working example of FIG. 2 a cortical bone thread 20. At its end facing the bone, a drill tip 5 is provided. The Kirschner wire 2b is inserted through a guide tube 4d. The guide tube 4d has a shaft 15b which is bounded on one end by the grip 12d. At the other end, a bevel 6 which is adapted to a corresponding recess of the implant 7 or of the aiming device 8 can be provided. The grip 12d serves predominantly for holding the guide tube 4 and for actuating it. Once again, a nut 3b is mounted on the Kirschner wire 2b.

Figures 3A, 3B:
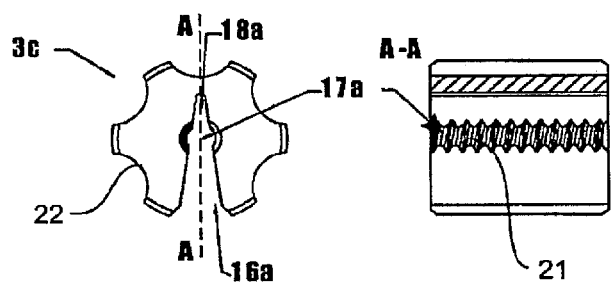
FIGS. 3A and 3B show a nut of the resetting tool in plan view (FIG. 3A) and in longitudinal section along the line A-A (FIG. 3B)
Figure 4:
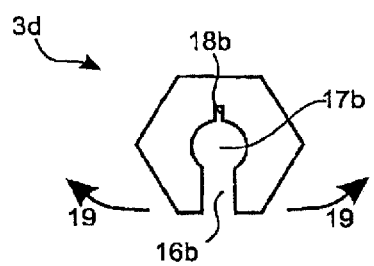
FIG. 4 shows a further working example of a nut in plan view.

FIGS. 3A, 3B and 4 each show a working example of a nut 3c and 3d, respectively. FIG. 3A shows a plan view and FIG. 3B shows a longitudinal section along the dashed line A-A in FIG. 3A. FIG. 4 shows a schematic plan view of the nut 3d. According to the invention, a longitudinal slot 16a, 16b is provided. This creates a passage to the inner bore 17a, 17b. The Kirschner wire 2 can now be pushed through this longitudinal slot 16a, 16b and is then present in the inner bore 17a, 17b. The nut may have an internal thread, in particular a bone thread or a metric thread. In FIG. 3B, a symmetrical thread 21 is shown. Both in the working example of FIGS. 3A, 3B and in that of FIG. 4, a recess 18a or 18b respectively, is provided opposite the longitudinal slot 16. Said recess generally has the form of an incision or slot. From a comparison of FIGS. 3A, 3B and 4, it is clear that the design of the recess 18 may vary. The recess 18 has a hinge function, so that the nut 3c, 3d can be spread in the region of the longitudinal slot 16a, 16b, indicated by the arrows 19 in FIG. 4. The spreading facilitates the mounting of the nut 3c, 3d on the Kirschner wire 2. From a comparison of FIGS. 3A, 3B and 4, it is furthermore evident that the longitudinal slot 16 may be differently designed. In FIGS. 3A and 3B, it is beveled so that the lateral introduction of the nut 3c onto the Kirschner wire 2 is facilitated.

The nut 3c moreover has recessed grips 22 which facilitate gripping of the nut 3c and hence the rotational movement thereof. However, the development of the sleeves is not limiting for the innovation.

Figure 5A:
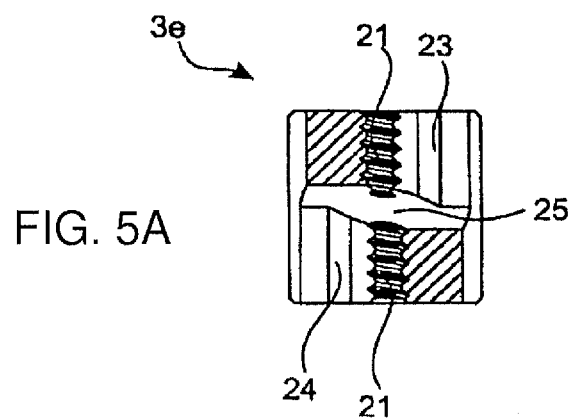
FIGS. 5A, 5B and 5C show yet another working example of a nut in longitudinal section (FIG. 5A) in side view (FIG. 5B) and in plan view (FIG. 5C).
Figure 5B:
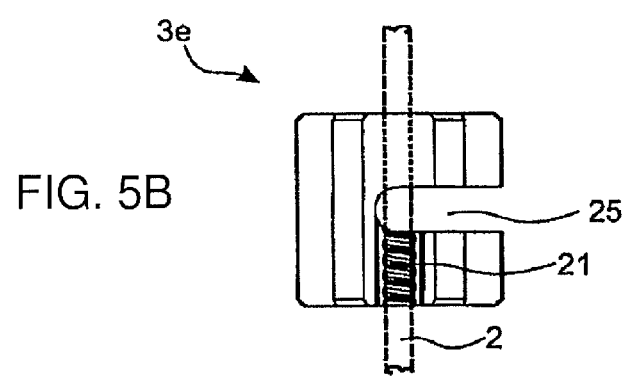
Figure 5C:
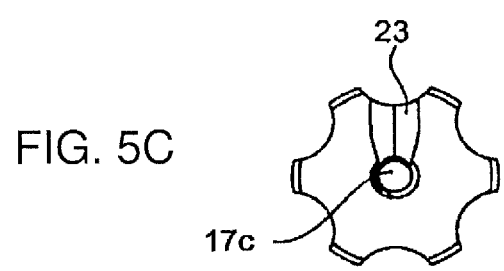

FIGS. 5A, 5B and 5C show a further working example of a nut 3e. Both a plan view (FIG. 5C) and a longitudinal section (FIG. 5A) and a side view are shown. The nut 3e once again has an inner bore 17c which may have a thread 21. Furthermore, it has a transverse slot 25 and a first and a second partial longitudinal slot 23, 24. As shown in particular in FIG. 5A, these slots are connected to one another. Furthermore, all slots are led to the inner bore 17c.

Once again, this creates a passage for the Kirschner wire 2. This is threaded in a bayonet-like manner. For this purpose, the nut 3e is first mounted with its transverse slot 25 onto the wire. The first mounting is thus effected 90° offset in comparison with the nut 3a-3d, which is shown in FIG. 1-4. There, the nut 3a-3d is mounted parallel to the longitudinal axis and hence to the inner bore 17. In the working example of FIGS. 5A, 5B and 5C, the nut 3e is mounted not parallel to the inner bore 17 but substantially perpendicularly thereto. Thereafter, the nut 3e is rotated through about 90° so that the Kirschner wire 2 now enters the partial longitudinal slots 23, 24. FIG. 5B shows, partly schematically, a Kirschner wire 2 which has been introduced. The dashed line represents the regions which are visible in the diagram; the dotted line represents that region of the wire which is not visible. By means of this design according to the invention, the nut 3e is safely guided on the Kirschner wire 2.

The transverse slot 25 can be arranged in particular approximately centrally. In this case, the partial longitudinal slots 22, 24 are longitudinal half-slots. However, this division can also be chosen otherwise, which is directly evident to the person skilled in the art.

LIST OF REFERENCE NUMERALS

1 Resetting tool
2 Kirschner wire
3 Nut
4 Guide tube
5 Drill tip
6 Bevel
7 Implant
8 Aiming device
9 Drill guide
10 Bore
11 Screw
12 Grip
13 14, 19 Arrow
15 Shaft
16 Longitudinal slot
17 Inner bore
18 Recess
20 Bone thread
21 Thread
22 Recessed grip
23 First partial longitudinal slot
24 Second partial longitudinal slot
25 Transverse slot

The invention claimed is:

1. A bone fixation system comprising:
an aiming device coupleable to an implant and including a guide hole which, when the aiming device is coupled to the implant, is aligned with an opening of the implant;
a guide tube extending along a first longitudinal axis from a first end to a second end and including a longitudinal bore extending therethrough along the first longitudinal axis, the second end sized and shaped to be inserted into the guide hole of the aiming device such that the first longitudinal axis is aligned with a central axis of the guide hole;
a Kirschner wire extending along a length and including a threaded portion along at least a portion of its length, the Kirschner wire configured and dimensioned for insertion through the longitudinal bore of the guide tube; and
a nut including therethrough along a second longitudinal axis thereof and having an outer perimeter, the nut configured and dimensioned for mounting over the Kirschner wire and including a threading extending along the internal bore to engage the threaded portion of the Kirschner wire,
wherein the nut is supported on the first end of the guide tube, and rotation of the nut about the second longitudinal axis axially displaces the Kirschner wire along the first longitudinal axis relative to the guide tube.

2. The system of claim 1, wherein the first and second longitudinal axes are parallel.

3. The system of claim 1, wherein the nut includes a lengthwise slot extending from the internal bore to the outer perimeter to permit the nut to be laterally mounted on the wire.

4. The system of claim 1, wherein the nut includes a transverse slot extending through the outer perimeter such that the nut has a generally C-shaped profile.

5. The system of claim 4, wherein the nut further includes first and second partial longitudinal slots which are connected to one another and to the transverse slot.

6. The system of claim 1, wherein the nut is formed of plastic.

7. The system of claim 1, wherein the threaded portion of the wire includes a bone thread.

8. The system of claim 7, wherein the bone thread is a cancellous thread or a cortical thread.

9. The system of claim 1, wherein the internal bore of the nut includes a thread portion.

10. The system of claim 9, wherein the threaded portion of the nut includes a symmetrical thread.

11. The system of claim 1, wherein the wire is threaded along its length.

12. The system of claim 3, wherein the internal bore of the nut includes a groove-like recess opposite the lengthwise slot.

13. The system of claim 3, wherein the internal bore of the nut includes a hinge opposite the lengthwise slot.

14. The system of claim 1, wherein the nut is configured to be destroyed by a sterilization process.

15. The system of claim 1, wherein the guide tube, wire and nut are configured for use with bone plates.

* * * * *